(12) United States Patent
Kumar et al.

(10) Patent No.: US 8,178,674 B2
(45) Date of Patent: May 15, 2012

(54) PROCESS FOR THE PREPARATION OF ZIPRASIDONE

(75) Inventors: Yatendra Kumar, Gurgaon (IN); Mohan Prasad, Gurgaon (IN); Mahivir Singh Khanna, New Delhi (IN); Seema Ahuja, Ghaziabad (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 13/100,833

(22) Filed: May 4, 2011

(65) Prior Publication Data

US 2011/0207933 A1    Aug. 25, 2011

Related U.S. Application Data

(62) Division of application No. 10/598,370, filed as application No. PCT/IB2005/000512 on Feb. 28, 2005, now abandoned.

(30) Foreign Application Priority Data

Feb. 27, 2004  (IN) .............................. 307/DEL/2004
Jul. 28, 2004  (IN) ............................ 1395/DEL/2004

(51) Int. Cl.
  *C07D 417/12*  (2006.01)
  *A61K 31/496*  (2006.01)
  *A61P 25/18*  (2006.01)

(52) U.S. Cl. .................................... 544/368; 514/254.02
(58) Field of Classification Search ......................... None
  See application file for complete search history.

(56) References Cited

U.S. PATENT DOCUMENTS

| | | | |
|---|---|---|---|
| 4,831,031 A | 5/1989 | Lowe, III et al. | 514/254 |
| 5,206,366 A | 4/1993 | Bowles | 544/368 |
| 5,312,925 A | 5/1994 | Allen et al. | 544/368 |
| 5,338,846 A | 8/1994 | Busch et al. | 544/368 |
| 6,110,918 A | 8/2000 | Busch et al. | 514/255 |
| 6,150,366 A | 11/2000 | Arenson et al. | 514/253 |
| 7,667,037 B2 * | 2/2010 | Pilarsky et al. | 544/366 |
| 2009/0047354 A1 | 2/2009 | Reddy et al. | 424/489 |

FOREIGN PATENT DOCUMENTS

| | | |
|---|---|---|
| EP | 0 584 903 | 3/1994 |
| EP | 0 586 191 | 3/1994 |
| EP | 0 965 343 | 12/1999 |
| WO | WO 03/070246 | 8/2003 |
| WO | WO 2004/050655 | 6/2004 |
| WO | WO 2004/089948 | 10/2004 |
| WO | WO 2005/016325 | 2/2005 |

* cited by examiner

*Primary Examiner* — Emily Bernhardt

(57) ABSTRACT

The invention relates to processes for the preparation of substantially pure ziprasidone. The invention also relates to the preparation of acid addition salts of ziprasidone. More particularly, it relates to the preparation of substantially pure hydrochloride salt of ziprasidone. The invention also relates to pharmaceutical compositions that include the substantially pure ziprasidone or ziprasidone hydrochloride and use of said compositions for treating schizophrenia.

21 Claims, No Drawings

PROCESS FOR THE PREPARATION OF ZIPRASIDONE

CROSS REFERENCE TO RELATED APPLICATION

This is a divisional application of U.S. application Ser. No. 10/598,370 filed Aug. 25, 2008.

FIELD OF THE INVENTION

The field of the invention relates to processes for the preparation of substantially pure ziprasidone. The invention also relates to the preparation of acid addition salts of ziprasidone. More particularly, it relates to the preparation of substantially pure hydrochloride salt of ziprasidone. The invention also relates to pharmaceutical compositions that include the substantially pure ziprasidone or ziprasidone hydrochloride and use of said compositions for treating schizophrenia.

BACKGROUND OF THE INVENTION

Chemically, ziprasidone is 5-[2-[4-(1,2-benzisothiazol-3-yl)-1-piperazinyl]ethyl]-6-chloro-1,3-dihydro-2H-indol-2-one having the structural Formula I. It is indicated for the treatment of schizophrenia. Ziprasidone is commercially available in the form of its hydrochloride salt.

FORMULA I

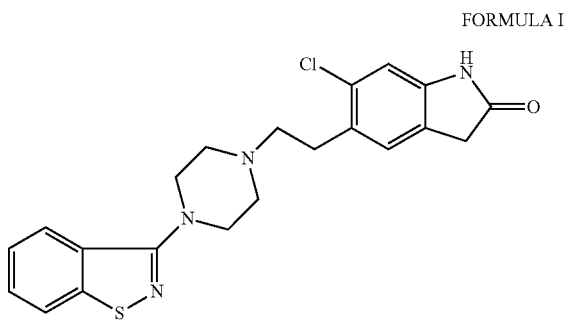

U.S. Pat. No. 4,831,031 discloses a process for the preparation of ziprasidone hydrochloride, which involves refluxing N-(1,2-benzisothiazol-3-yl)piperazine with 5-(2-chloroethyl)-6-chloro-oxindole in methyl isobutyl ketone in the presence of sodium iodide and sodium carbonate for about 40 hours followed by column chromatographic purification of the product to get ziprasidone base which is dissolved in methylene chloride and treated with ethereal hydrogen chloride to get ziprasidone hydrochloride salt. The salt is washed with acetone and the product is dried.

U.S. Pat. No. 5,312,925 discloses a process for the preparation of ziprasidone hydrochloride, which involves heating to reflux a mixture of 5-(2-chloroethyl)-6-chloro-oxindole and 1-(1,2-benzisothiazol-3-yl)piperazine in aqueous sodium carbonate for 14 hours, followed by cooling to 20° C. and filtration. The wet product is re-slurried in isopropyl alcohol and filtered, washed with fresh isopropyl alcohol followed by drying under vacuum to get ziprasidone base. The base is then treated with aqueous hydrochloric acid in the presence of water at a temperature of about 60-65° C. for 3 to 24 hours, followed by filtration, washing with water and drying under vacuum to get ziprasidone hydrochloride.

U.S. Pat. Nos. 5,206,366 and 5,338,846 disclose a process for the preparation of ziprasidone base, which involves heating to reflux a mixture of 5-(2-chloroethyl)-6-chloro-oxindole and 1-(1,2-benzisothiazol-3-yl)piperazine in aqueous sodium carbonate for 13 hours followed by cooling to 25° C. and filtration. The product is re-slurried in isopropyl alcohol twice and then filtered and dried under vacuum. The dried product is recrystallized from tetrahydrofuran to get ziprasidone base having a purity of 99.7% measured by HPLC.

U.S. Pat. No. 6,150,366 discloses a process for the preparation of ziprasidone hydrochloride from double recrystallized ziprasidone base having a purity of about 99.7% by HPLC. The process involves refluxing a slurry of ziprasidone base in tetrahydrofuran and water to get a clear solution followed by addition of aqueous hydrochloric acid solution at 60-62° C. in two lots, cooling the mixture to 13° C. to complete crystallization of ziprasidone hydrochloride. The product is filtered and washed with fresh cold tetrahydrofuran.

The prior art approach for the preparation of ziprasidone or a pharmaceutically acceptable salt thereof is not suitable from a commercial point of view because the product is not obtained in high purity and is not color stable, thus making the approach commercially difficult to implement. The purity hereto refers to the compound purity.

To achieve a high efficiency of reaction for industrial scale synthesis of ziprasidone hydrochloride, it is necessary to minimize the formation of the impurities.

The present inventors have found that these problems associated with prior art could be attributed to non-effective removal of trapped hydrogen chloride from the reaction product. The entrapped hydrogen chloride leads to degradation of ziprasidone hydrochloride and leads to the formation of the impurities, which both darken the color and increase the impurity content. These impurities have been identified in the product as isopropylene ziprasidone and mesityl oxide impurities.

Thus, the present invention provides a process which does not result in impure ziprasidone or a pharmaceutically acceptable salt thereof; rather pure ziprasidone having impurity less than 0.1% is obtained. The ziprasidone hydrochloride when made by the process of the present invention is color stable and easy to handle thus making the process amenable for commercial scale use.

SUMMARY OF THE INVENTION

In one general aspect there is provided a process for the preparation of ziprasidone base of Formula I, or a salt thereof.

FORMULA I

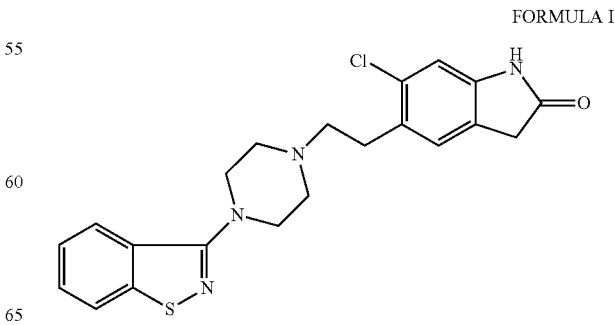

The process includes reacting a compound of Formula II,

FORMULA II

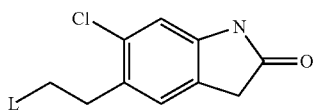

wherein L is a leaving group, with 1-(1,2-benzisothiazol-3-yl)piperazine of Formula III,

FORMULA III

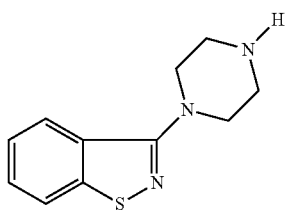

in water in absence of a base to form a mixture, heating the resultant mixture to from about 50° C. to reflux temperature, and isolating the ziprasidone base of Formula I, or a salt thereof.

The leaving group may be a conventional leaving group, for example chloro, bromo, iodo, mesyloxy, tosyloxy or acetyloxy, and the like.

The process may include further drying of the product obtained.

In another general aspect there is provided a substantially pure ziprasidone of Formula I having a purity of more than 99.8% with total impurities less than 0.2% by HPLC.

In another general aspect there is provided a process for the preparation of substantially pure ziprasidone. The process includes obtaining a suspension of ziprasidone in one or more solvents; heating the suspension to get a clear solution; and recovering the substantially pure ziprasidone by the removal of the solvent.

The solvent may be one or more of lower alkanols, ethers, ketones, chlorinated hydrocarbons, polar aprotic solvents, water, or mixtures thereof. The lower alkanol may include one or more of primary, secondary and tertiary alcohol having from one to six carbon atoms. The lower alkanol may include one or more of methanol, ethanol, n-propanol, and isopropanol.

The ketone may include one or more of acetone, ethyl methyl ketone, methyl isobutyl ketone, and diisobutyl ketone.

The ether may include one or both of tetrahydrofuran and 1,4-dioxane. A suitable chlorinated hydrocarbon includes one or more of chloroform, dichloromethane, and 1,2-dichloroethane.

The polar aprotic solvent may include one or more of N,N-dimethylformamide, N,N-dimethylacetamide, dimethylsulphoxide, acetonitrile, and N-methylpyrrolidone.

Removing the solvent may include, for example, one or more of distillation, distillation under vacuum, evaporation, filtration, filtration under vacuum, decantation and centrifugation.

The ziprasidone may be recovered from the solution by filtration, filtration under vacuum, decantation or centrifugation. The process may include further forming of the product so obtained into a finished dosage form.

The ziprasidone can also be recovered from the solution by adding a suitable additional solvent/second solvent resulting in the precipitation of the substantially pure ziprasidone and removing the solvent there from by filtration, filtration under vacuum, decantation or centrifugation.

The process may include further drying of the product obtained.

In one general aspect, the solution may be cooled before filtration to obtain better yields of the substantially pure ziprasidone, or a salt thereof.

The process may produce the substantially pure ziprasidone having a purity of more than 99.8% with total impurities less than 0.2% by HPLC. In particular, it may produce the pure ziprasidone having a purity of more than 99.9% with total impurities less than 0.1%.

In another general aspect there is provided a process for preparing ziprasidone hydrochloride. The process includes obtaining a suspension of ziprasidone in one or more solvents; contacting the suspension with hydrogen chloride; and isolating the ziprasidone hydrochloride in substantially pure form.

In another general aspect there is provided a pharmaceutical composition that includes a therapeutically effective amount of substantially pure ziprasidone hydrochloride and one or more pharmaceutically acceptable carriers, excipients or diluents.

In another general aspect there is provided a method for treating schizophrenia in a warm-blooded animal, the method comprising providing a pharmaceutical composition to the warm-blooded animal that includes the substantially pure ziprasidone hydrochloride.

The details of one or more embodiments of the inventions are set forth in the description below. Other features, objects and advantages of the inventions will be apparent from the description and claims.

DETAILED DESCRIPTION OF THE INVENTION

The inventors have developed processes for the preparation of ziprasidone base, or a salt thereof, by reacting a compound of Formula II,

FORMULA II

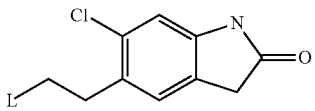

wherein L is a leaving group, with 1-(1,2-benzisothiazol-3-yl)piperazine of Formula III,

FORMULA III

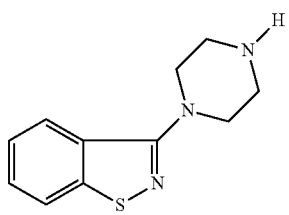

in water in absence of a base to form a mixture, heating the resultant mixture to from about 50° C. to reflux temperature, and isolating the ziprasidone base of Formula I, or a salt thereof.

In general, the reaction of the compound of Formula II and compound of Formula III may be carried out in water only. Alternatively, the reaction may be carried out in the presence of water and an organic solvent. The reaction mixture may be heated at a temperature of from about 50° C. to reflux temperature. The process may produce the ziprasidone having a purity of more than 97% by HPLC.

In one aspect, the reaction mass after completion of reaction (as monitored by HPLC) may be filtered. The filtration may be carried out at a temperature of about 40° C. to about 100° C.

In another aspect, the wet product obtained may be suspended in de-ionized water, a suitable solvent, or both. The wet product may be suspended at room temperature to a temperature of about 100° C. The suspension may be cooled before isolating to get ziprasidone base of Formula I, or a salt thereof.

The leaving group L present in the compound of Formula II may be a conventional leaving group known to a person of ordinary skills in the art, including, for example, chloro, bromo, iodo, mesyloxy, tosyloxy or acetyloxy and the like.

The organic solvent includes one or more of alcohols, ketones, ethers, polar aprotic solvents, esters, or mixtures thereof. A suitable alcohol includes one or more of methanol, ethanol, n-propanol, isopropanol, n-butanol, isobutanol, and tert-butanol. Examples of ketones include acetone, methyl isobutyl ketone and ethyl methyl ketone. Examples of ethers include solvents such as tetrahydrofuran and 1,4-dioxane. Examples of polar aprotic solvents include solvents such as N,N-dimethylacetamide, N,N-dimethylformamide, acetonitrile, and N-methylpyrrolidone. Examples of esters include methyl acetate, ethyl acetate, and isopropyl acetate. Mixtures of all of these solvents are also contemplated.

The inventors also have developed a process for the preparation of substantially pure ziprasidone base, by obtaining a suspension of ziprasidone in one or more solvents; heating the suspension to get a clear solution; and recovering the substantially pure ziprasidone by the removal of the solvent.

The ziprasidone base may be prepared as described above or may be prepared by any of the methods known in the art, including those described in U.S. Pat. Nos. 4,831,031; 5,312,925; 5,206,366; and 5,338,846.

The term "solvent" includes one or more of lower alkanols, ethers, ketones, chlorinated hydrocarbons, polar aprotic solvents, water, or mixtures thereof. Examples of alkanol include those primary, secondary and tertiary alcohols having from one to six carbon atoms. Suitable lower alkanol solvents include methanol, ethanol, n-propanol, and isopropanol. Examples of ketones include solvents such as acetone, ethyl methyl ketone, methyl isobutyl ketone, and diisobutyl ketone. Examples of ethers include tetrahydrofuran and 1,4-dioxane. Examples of chlorinated hydrocarbon include solvents such as chloroform, dichloromethane, and 1,2-dichloroethane. A suitable polar aprotic solvent includes one or more of N,N-dimethylformamide, N,N-dimethylacetamide, dimethylsulphoxide, acetonitrile, and N-methylpyrrolidone. Mixtures of all of these solvents are also contemplated.

The solution of ziprasidone in a solvent can be obtained by dissolving, slurrying, stirring, or a combination thereof. The solution of ziprasidone may be obtained by heating the solvent. It may be heated from about 40° C. to reflux temperature. The solution of ziprasidone can also be obtained by adding water and heating.

The solvent may be removed from the solution by a technique which includes, for example, distillation, distillation under vacuum, evaporation, filtration, filtration under vacuum, decantation and centrifugation.

In one aspect, the solution may be cooled before filtration to obtain better yields.

The product obtained may be further or additionally dried to achieve the desired moisture values. For example, the product may be further or additionally dried in a tray drier, dried under vacuum and/or in a Fluid Bed Dryer.

The substantially pure ziprasidone base has a purity of more than 99.8% with total impurities less than 0.2% when determined by HPLC. More particularly, the purity of ziprasidone base is more than 99.9% with total impurities less than 0.1% by HPLC.

The inventors also have developed a process for the preparation of the substantially pure ziprasidone hydrochloride, by obtaining a suspension of ziprasidone in one or more solvents; contacting the solution with hydrogen chloride to form a solid; isolating the ziprasidone hydrochloride in substantially pure form. The inventors also have developed pharmaceutical compositions that contain the substantially pure ziprasidone hydrochloride, in admixture with one or more solid or liquid pharmaceutical diluents, carriers, and/or excipients.

The organic solvent may include one or more of chlorinated hydrocarbons, aromatic hydrocarbons, polar aprotic solvents, ethers, ketones, lower alcohols or mixtures thereof. Examples of chlorinated hydrocarbons include methylene chloride, chloroform, and ethylene chloride. Examples of aromatic hydrocarbons include solvents such as toluene, xylene, and substituted toluenes. A suitable polar aprotic solvent includes one or more of acetonitrile, N,N-dimethylformamide, N,N-dimethylacetamide, and dimethylsulphoxide. Examples of ethers include tetrahydrofuran, 1,4-dioxane, diethyl ether, diisopropyl ether, and methyl tert-butyl ether. Examples of ketone include solvents such as acetone, ethyl methyl ketone, diisobutyl ketone, and methyl isobutyl ketone. Suitable lower alcohols include methanol, ethanol, n-propanol, isopropanol, n-butanol, isobutanol, and tert-butanol. Mixtures of all of these solvents are also contemplated.

In general, the hydrogen chloride may be added to a suspension of ziprasidone in a suitable solvent. Alternatively, the hydrogen chloride may be added in the last step for the preparation of substantially pure ziprasidone base and ziprasidone hydrochloride in substantially pure form may be isolated directly.

The hydrogen chloride used in the salt formation may be an aqueous solution or in gaseous form. The aqueous solution of hydrogen chloride is commercially available. The gaseous hydrogen chloride may be obtained commercially or prepared by the methods known in the art. The gaseous hydrogen chloride may be dissolved in a suitable solvent.

The ziprasidone base may be treated with hydrogen chloride in the presence of an organic solvent at a temperature of from about 50° C. to reflux temperature.

Isolating the ziprasidone hydrochloride in the substantially pure form includes one or more of washing, crystallization, precipitation, cooling, filtration, filtration under vacuum, decantation and centrifugation.

The wet product may be washed with water and/or a suitable organic solvent, including, for example, lower alkanols, ethers, polar aprotic solvents, or mixtures thereof. The product may be washed till the washings are free of acidity. Such washings can be accomplished while the product is in centrifuge or in suitable filter or in a reaction vessel. Washing the product can be carried out at a lower temperature using pre-cooled washing solvents as mentioned above. Examples of polar aprotic solvents include N,N-dimethylformamide, 1,4-dioxane, acetonitrile, tetrahydrofuran and N,N-dimethylacetamide. Examples of alkanols include methanol, ethanol, n-propanol, isopropyl alcohol and t-butanol. A suitable ether includes one or more of diethyl ether, diisopropyl ether, methyl t-butyl ether and petroleum ether.

After ensuring the complete removal of trapped acidity, the product is isolated and optionally dried under vacuum at about 35 to 55° C. to get ziprasidone hydrochloride.

The process may produce the substantially pure ziprasidone hydrochloride having a purity of more than 99.8% with total impurities less than 0.2% by HPLC. In particular, it may produce the pure ziprasidone hydrochloride having a purity of more than 99.9% with total impurities less than 0.1%.

The resulting pure ziprasidone hydrochloride may be formulated into ordinary dosage forms such as, for example, tablets, capsules, pills, solutions, etc. In these cases, the medicaments can be prepared by conventional methods with conventional pharmaceutical excipients.

The compositions include dosage forms suitable for oral, buccal, rectal, and parenteral (including subcutaneous, intramuscular, and ophthalmic) administration. The oral dosage forms may include solid dosage forms, like powder, tablets, capsules, suppositories, sachets, troches and lozenges as well as liquid suspensions, emulsions, pastes and elixirs. Parenteral dosage forms may include intravenous infusions, sterile solutions for intramuscular, subcutaneous or intravenous administration, dry powders to be reconstituted with sterile water for parenteral administration, and the like.

The substantially pure form of ziprasidone hydrochloride can be administered for the treatment of schizophrenia, in a warm-blooded animal.

For the purpose of this disclosure, a warm-blooded animal is a member of the animal kingdom possessed of a homeostatic mechanism and includes mammals and birds.

The present invention is further illustrated by the following examples which are provided merely to be exemplary of the invention and do not limit the scope of the invention. Certain modifications and equivalents will be apparent to those skilled in the art and are intended to be included within the scope of the present invention.

EXAMPLE 1

Preparation of Ziprasidone Base

To de-ionized water (2.0 Lit), was added 5-(2-chloroethyl)-6-chloro-oxindole (100 g) and 1-(1,2-benzisothiazol-3-yl) piperazine (210 g) at 30-35° C. The mixture was slowly heated under stirring to 98-100° C. over 60-80 minutes. The resultant mass was stirred for 10-15 hours at 98-100° C. After completion of reaction as monitored by HPLC, the suspended solid material was filtered at 98-100° C. The wet cake so obtained was suspended in de-ionized water (2.0 Lit) and heated to 90-95° C. and maintained at this temperature for 30 minutes. The solid suspension was filtered at 90-95° C. The wet cake was further added to isopropyl alcohol (1.5 Lit) and stirred for 2 hours at 30-35° C. The solids were filtered and washed with isopropyl alcohol (500 ml) and dried under vacuum at 50-55° C. for 7-8 hours till moisture content was not more than 1.0% w/w.
Yield: 145 g (82%)
Purity: greater than 97.0% by HPLC

EXAMPLE 2

Preparation of Ziprasidone Base

To de-ionized water (1.5 Lit), was added 5-(2-bromoethyl)-6-chloro-oxindole (75 g) and 1-(1,2-benzisothiazol-3-yl)piperazine (132 g) at 30-35° C. The mixture was slowly heated under stirring to 98-100° C. over 60-80 minutes. The resultant mass was stirred for 4-5 hours at 98-100° C. After completion of reaction as monitored by HPLC, the suspended solid material was filtered at 98-100° C. The wet cake so obtained was suspended in de-ionized water (1.5 Lit) and heated to 90-95° C. and further maintained at this temperature for 30 minutes. The solid suspension was filtered at 90-95° C. The wet cake was further added to isopropyl alcohol (1.5 Lit) and the resultant mass was heated to reflux and maintained at reflux for 1 hour. The mass was further cooled to 30-35° C. and stirred for 2 hours at 30-35° C. The solids were filtered and washed with isopropyl alcohol (75 ml) and dried under vacuum at 50-55° C. for 7-8 hours till moisture content was not more than 1.0% w/w.
Yield: 96.5 g (85%)
Purity: greater than 97.0% by HPLC

EXAMPLE 3

Preparation of Substantially Pure Ziprasidone Base

To de-ionized water (1.5 Lit), was added 5-(2-bromoethyl)-6-chloro-oxindole (75 g) and 1-(1,2-benzisothiazol-3-yl)piperazine (132 g) at 30-35° C. The mixture was slowly heated under stirring to 98-100° C. over 60-80 minutes. The resultant mass was stirred for 4-5 hours at 98-100° C. After completion of reaction as monitored by HPLC, the suspended solid material was filtered at 98-100° C. The wet cake so obtained was suspended in de-ionized water (1.5 Lit) and heated to 90-95° C. and further maintained at this temperature for 30 minutes. The solid suspension was filtered at 90-95° C. The wet cake was further added to isopropyl alcohol (1.5 Lit) and the resultant mass was heated to reflux and maintained at reflux for 1 hour. The mass was further cooled to 30-35° C. and stirred for 2 hours at 30-35° C. The solids were filtered and washed with isopropyl alcohol (75 ml) and dried under vacuum at 50-55° C. for 7-8 hours till moisture content was not more than 1.0% w/w.

The product so obtained was suspended in tetrahydrofuran (2.37 Lit) and heated to reflux at 65-67° C. The resultant mass was maintained under reflux for 10-15 minutes. De-ionized water (190 ml) was added at 65-67° C. and further stirred under reflux at 65-67° C. for 15-20 minutes to get a clear solution. Activated carbon (9.5 g) was added to the clear solution at 65-67° C. with stirring for 1 hour at 65-67° C. The reaction mass was filtered while hot under vacuum through celite bed at 65-67° C. The celite bed was washed with tetrahydrofuran (190 ml). The solvent was recovered under vacuum at 50-55° C. leaving behind about 78 ml of the reaction mass. The resultant suspension was cooled slowly under stirring to 35° C. and maintained for further 30 minutes. It was further cooled to 3-5° C. and maintained for 2 hours under stirring at 3-5° C. The solid separated was filtered and the wet cake was slurry washed with isopropyl alcohol (285 ml). The product was then dried under vacuum at 50-55° C. for 7-8 hours till the moisture was less than 0.5% w/w.
Yield: 67 g (71%)
Purity: greater than 99.75% by HPLC
Impurity: Total impurities not more than 0.25% by HPLC

EXAMPLE 4

Preparation of Substantially Pure Ziprasidone Hydrochloride

To substantially pure ziprasidone base (100 g), was added dichloromethane (2.0 Lit) and stirred for 15-20 minutes at 30-35° C. To this, ethereal solution of hydrogen chloride (95.7 ml) was added over a period of 5-10 min at 30-35° C. under stirring. The suspension was further stirred for 17-20 hours at 32-35° C. and separated solids were filtered under vacuum and nitrogen atmosphere at 32-35° C. The wet solid was washed with diethyl ether (100 ml). The wet cake so obtained was suspended in acetone (500 ml) at 30-35° C. and stirred for 15-20 minutes at 30-35° C. The solid was filtered, washed with acetone (0.20 Lit) and dried under vacuum at 55-60° C. for 12-15 hours till the moisture content was not more than 0.5% w/w.
Yield: 105 g (94%)
Moisture content by Karl Fischer: Less than 0.5% w/w
Purity: greater than 99.9% by HPLC.
Impurity: Total impurities not more than 0.1% by HPLC

EXAMPLE 5

Preparation of Ziprasidone Base

To de-ionized water (1.5 Lit), was added 5-(2-bromoethyl)-6-chloro-oxindole (75 g) and 1-(1,2-benzisothiazol-3-yl)piperazine (132 g) at 30-35° C. The mixture was slowly heated under stirring to 98-100° C. over 60-80 minutes. The resultant mass was stirred for 4-5 hours at 98-100° C. After completion of reaction as monitored by HPLC, the suspended solid material was filtered at 98-100° C. The wet cake so obtained was suspended in de-ionized water (1.5 Lit) and heated to 90-95° C. and further maintained at this temperature for 30 minutes. The solid suspension was filtered at 90-95° C. and the wet cake was further added to isopropyl alcohol (1.5 Lit). The resultant mass was heated to reflux and maintained at reflux for 1 hour. The mass was further cooled to 30-35° C. and stirred for 2 hours at 30-35° C. The solids were filtered and washed with isopropyl alcohol (75 ml) and dried under vacuum at 50-55° C. for 7-8 hours till moisture content was not more than 1.0% w/w.

The product obtained was suspended in tetrahydrofuran (2.37 Lit) and heated to reflux (65-67° C.). The resultant mass was maintained under reflux for 10-15 minutes. De-ionized water (190 ml) was added at 65-67° C. and further stirred under reflux at 65-67° C. for 15-20 minutes to get a clear solution. Activated carbon (9.5 g) was added to the clear solution at 65-67° C. with stirring for 1 hour at 65-67° C. The reaction mass was filtered while hot under vacuum through celite bed at 65-67° C. The celite bed was washed with tetrahydrofuran (190 ml). The solvent was recovered under vacuum at 50-55° C. leaving behind about 78 ml of the reaction mass. The resultant suspension was cooled under stirring slowly to 35° C. and maintained for further 30 minutes. It was further cooled to 3-5° C. and maintained for 2 hours under stirring at 3-5° C. The solid separated was filtered and the wet cake was slurry washed with isopropyl alcohol (285 ml). The product was then dried under vacuum at 50-55° C. for 7-8 hours till the moisture was less than 0.5% w/w.
Yield: 67 g (71%)
Purity: greater than 99.75% by HPLC
Impurity: Total impurities not more than 0.25% by HPLC

EXAMPLE 6

Preparation of Ziprasidone Hydrochloride

To substantially pure ziprasidone base (100 g), was added dichloromethane (2.0 Lit) and stirred for 15-20 minutes at 30-35° C. To this, was added ethereal solution of hydrogen chloride (95.7 ml) over a period of 5-10 min at 30-35° C. under stirring. The suspension was further stirred for 17-20 hours at 32-35° C. and separated solids were filtered under vacuum and nitrogen atmosphere at 32-35° C. The wet solid was washed with diethyl ether (100 ml) and was suspended in water (500 ml) at 20-25° C. It was stirred for 30 minutes at 20-25° C. The mass was filtered and re-suspended in water (500 ml) and after stirring for approximately 1 hour, the cake was filtered and washed with a pre-cooled mixture of water and isopropanol (2×250 ml, 1:0.25). The washings were found to be free of acidity (pH of about 7). The product obtained was dried under vacuum at 55-60° C. for 12-15 hours till the moisture content was less than 0.5% w/w.
Yield: 105 g (94%)
Moisture content by Karl Fischer: Less than 0.5% w/w
Purity: greater than 99.9% by HPLC.
Impurity: Total impurities not more than 0.1% by HPLC

EXAMPLE 7

Preparation of Ziprasidone Base

To de-ionized water (4.0 Lit), was added 5-(2-chloroethyl)-6-chloro-oxindole (200 g) and 1-(1,2-benzisothiazol-3-yl)piperazine (419.8 g) at 30-35° C. The mixture was slowly heated under stirring to 98-100° C. over 60-90 minutes. The resultant mass was stirred for 12-15 hours at 98-100° C. After completion of reaction as monitored by HPLC, the suspended solid material was filtered at 98-100° C. The wet cake so obtained was suspended in de-ionized water (4.0 Lit) and heated to 90-95° C. and further maintained at this temperature for 30 minutes. The solid suspension was filtered at 90-95° C. The wet cake was further added to isopropyl alcohol (3.0 Lit) and the resultant mass was heated to reflux and maintained at reflux for 1 hour. The mass was further cooled to 30-35° C. and stirred for 1 hour at 30-35° C. The solids were filtered and washed with isopropyl alcohol (1.0 Lit) and dried under vacuum at 50-55° C. for 10-12 hours till moisture content was not more than 1.0% w/w.

The product so obtained was suspended in tetrahydrofuran (7.3 Lit) and de-ionized water (580 ml) and heated to reflux (65-67° C.). The resultant mass was maintained under reflux for 10-15 minutes at 65-67° C. and further stirred under reflux at 65-67° C. for 40-45 minutes to get a clear solution. Activated carbon (29 g) was added to the clear solution at 65-67° C. with stirring for 1 hour at 65-67° C. The reaction mass was filtered while hot under vacuum through celite bed at 65-67° C. The celite bed was washed with tetrahydrofuran (580 ml). The solvent was recovered under vacuum at 50-55° C. leaving behind about 2.2 Lit of the reaction mass. The resultant suspension was cooled under stirring slowly to 35° C. and maintained for further 30 minutes. It was further cooled to 3-5° C. and maintained for 2 hours under stirring at 3-5° C. The solid separated was filtered and the wet cake was slurry washed with isopropyl alcohol (870 ml). The product was then dried under vacuum at 50-55° C. for 7-8 hours till the moisture was less than 0.5% w/w.
Yield: 267 g (68%)
Purity: 99.96% by HPLC
Impurity: Single known or unknown impurity 0.03% by HPLC

EXAMPLE 8

Preparation of Ziprasidone Hydrochloride

To substantially pure ziprasidone base (100 g), was added dichloromethane (2.0 Lit) and stirred for 15-20 minutes at 25-30° C. To the mixture so obtained, ethereal solution of hydrogen chloride (135 ml) was added over a period of 5-10 min at 25-30° C. under stirring. The suspension was further stirred for 17-20 hours at 25-30° C. and separated solids were filtered under vacuum and nitrogen atmosphere at 30-35° C. The wet solid was washed with diethyl ether (100 ml). The wet cake was suspended in water (500 ml) at 20-25° C. and stirred for 30 minutes at 20-25° C. The mass was filtered and re-suspended in water (500 ml) and after stirring for approximately 1 hour, filtered and the cake was washed with a pre-cooled mixture of water and isopropanol (2×250 ml, 1:0.25). The washings were found to be free of acidity (pH of about 7). The product obtained was dried under vacuum at 55-60° C. for 12-15 hours till the moisture content was less than 0.5% w/w.

Yield: 105 g (94%)

Moisture content by Karl Fischer: Less than 0.5% w/w

Purity: 99.91% by HPLC.

Impurity: Isopropylene ziprasidone 0.09% by HPLC

While the present invention has been described in terms of its specific embodiments, certain modifications and equivalents will be apparent to those skilled in the art and are included within the scope of the present invention.

We claim:

1. A process for the preparation of ziprasidone hydrochloride, comprising the steps of
   (a) reacting a compound of Formula II,

FORMULA II

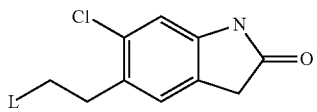

wherein L is a leaving group, with 1(1,2-benzisothiazol-3-y)piperazine of Formula III,

FORMULA III

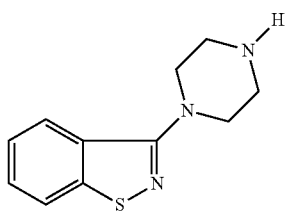

in water in absence of a base to form a mixture;
   (b) heating the resultant mixture to from about 50° C. to reflux temperature in an organic solvent;
   (c) isolating the ziprasidone base of Formula I,

FORMULA I

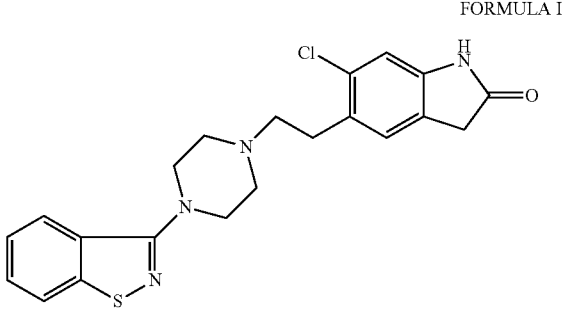

(d) obtaining a first suspension of ziprasidone of Formula I in a solvent; heating the first suspension to get a clear solution; and recovering the substantially pure ziprasidone by the removal of the first solvent; and
   (e) obtaining a second suspension of substantially pure ziprasidone in a solvent; contacting the second suspension with hydrogen chloride to form a solid; and isolating ziprasidone hydrochloride in substantially pure form.

2. A process according to claim 1, wherein the leaving group L in step (a) is selected from the group consisting of chloro, bromo, iodo, mesyloxy, tosyloxy and acetyloxy.

3. A process according to claim 1, wherein the organic solvent in step (b) is selected from the group consisting of alcohols, ketones, polar aprotic solvents, esters, and mixtures thereof.

4. A process according to claim 1, wherein the solvent in step (c) is selected from the group consisting of lower alkanols, ethers, ketones, chlorinated hydrocarbons, polar aprotic solvents, water, and mixtures thereof.

5. A process according to claim 4, wherein the lower alkanol comprises one or more of methanol, ethanol, n-propanol, and isopropanol.

6. A process according to claim 4, wherein the ether comprises one or both of tetrahydrofuran, and 1,4-dioxane.

7. A process according to claim 4, wherein the ketone comprises one or more of acetone, ethyl methyl ketone, methyl isobutyl ketone, and diisobutyl ketone.

8. A process according to claim 4, wherein the chlorinated hydrocarbon comprises one or more of chloroform, dichloromethane, and 1,2-dichloroethane.

9. A process according to claim 4, wherein the polar aprotic solvent is selected from N,N-dimethylformamide, N,N-dimethylacetamide, dimethylsulfoxide, acetonitrile, or N-methylpyrrolidone.

10. A process according to claim 1, wherein the first suspension is heated from about 40° C. to reflux temperature.

11. A process according to claim 1, wherein removing the solvent in step (c) involves at least one of the techniques selected from distillation, distillation under vacuum, evaporation, filtration, filtration under vacuum, decantation, and centrifugation.

12. A process according to claim 11, further comprising adding additional solvent in step (c) before removing the solvent.

13. A process according to claim 1, wherein the substantially pure ziprasidone in step (c) is recovered from the solution by distillation.

14. A process according to claim 13, wherein the distillation is carried out under vacuum.

15. A process according to claim 1, wherein the substantially pure ziprasidone in step (c) is recovered from the solution by filtration.

16. A process according to claim 1, further comprising additional drying of the substantially pure ziprasidone obtained in step (c).

17. A process according to claim 1, further comprising cooling before removing the solvent in step (c).

18. A process according to claim 1, wherein the solvent in step (d) is selected from the group consisting of lower alkanols, chlorinated hydrocarbons, aromatic hydrocarbons, polar aprotic solvents, ethers, ketones, and mixtures thereof.

19. A process according to claim 1, wherein the solid obtained in step (d) is washed with water, a polar aprotic solvent, a lower alkanol, an ether, or mixtures thereof before isolation.

20. A process according to claim 19, wherein the washing is done till the washings are free of any acidity.

21. A process according to claim 1, further comprising additional drying of the product ziprasidone hydrochloride obtained in step (e).

* * * * *